Hollander et al. [45] Date of Patent: Apr. 28, 1987

[54] DENATONIUM SACCHARIDE COMPOSITIONS AND METHOD OF USE

[75] Inventors: Gary T. Hollander, Obetz, Ohio; Mel Blum, New York, N.Y.

[73] Assignee: Atomergic Chemetals Corporation, Plainview, N.Y.

[21] Appl. No.: 667,924

[22] Filed: Nov. 2, 1984

[51] Int. Cl.$^4$ .......................................... C07D 275/00
[52] U.S. Cl. .................................... 514/373; 548/210; 514/920
[58] Field of Search ...................... 548/211, 212, 210; 514/373

[56] References Cited

U.S. PATENT DOCUMENTS 2,725,326 11/1955 Shibe et al. .......................... 548/211
3,923,997 12/1975 Meulyi ................................. 514/460
4,064,316 12/1977 Curtis et al. ............................ 424/2
4,235,891 11/1980 Saito et al. ........................... 514/144

FOREIGN PATENT DOCUMENTS 391243 2/1984 Japan .................................... 548/211

OTHER PUBLICATIONS (Annon.), "Denatonium Benzoate as Deterrent for Ingestion," C.A. 97: 50752(c) (1982).
Bartoshuk, Linda, "Bitter Taste of Saccharin Related to the Genetic Ability . . . , " C.A. 91: 13835(h) (1979).
Saroli, A., "Structure-Activity Relationship of a Bitter Compound . . . , " Chem. Abst. 101: 169274(g) (1984).

*Primary Examiner*—Donald G. Daus
*Assistant Examiner*—G. M. Hendricks
*Attorney, Agent, or Firm*—Jordan & Hamburg

[57] ABSTRACT

A composition consisting essentially of an effective amount of denatonium saccharide which has a vile, bitter taste, a solvent which provides the composition with the capability of penetrating the surface of an article to be protected, and an inert material, is applied to protect an article from gnawing, biting, licking and feeding by various animals.

12 Claims, No Drawings

DENATONIUM SACCHARIDE COMPOSITIONS AND METHOD OF USE

BACKGROUND OF THE INVENTION AND PRIOR ART STATEMENT

This invention relates to denatonium saccharide compositions and methods for use as animal and rodent repellents. (Rodents are, of course, a class of animal and are highlighted here due to their gnawing; the term "animal" as used herein is also intended to include birds, of which woodpeckers can, for example, be a particular problem).

The literature has described only the bitter tasting property of denatonium benzoate, and its use as a denaturing substance for alcohol and paint formulations, and as a deterrent in animal compositions. Such references include U.S. Pat Nos. 3,080,326; 3,080,327; 3,268,577; 3,935,137; 4,005,038; and 4,064,316; German Pat. Nos. 2,642,606; 2,942,537 and 2,942,581; British Pat. No. 866,605; and Europat No. 12,525.

Since it has been discovered, as described in the copending application of the same inventors, "Denatonium Saccharide Compositions and Methods of Use," Ser. No. 667,776 filed simultaneously herewith, that denatonium saccharide is five times more bitter than denatonium benzoate, it is desired to provide new and improved denatonium saccharide compositions and methods of use.

Accordingly, it is the object of this invention to provide novel compositions for utilizing the bitter tasting property of denatonium saccharide at low concentrations, which compositions include a solvent which is capable of being applied to and penetrate various surfaces to thereby provide protection of the surface against attack by animals and rodents.

SUMMARY OF THE INVENTION

In accordance with an object of the invention, there is provided herein a composition for utilizing the bitter tasting property of denatonium saccharide at low concentrations. The composition consists essentially of an effective amount of denatonium saccharide, a solvent which provides the composition with the capability of penetrating the surface of an article to be protected, and an inert material.

In a preferred embodiment of the invention the denatonium saccharide is present in an amount of about 0.001 to 0.5% by weight of the composition, the solvent is dimethylsulfoxide or 2,4-dimethylsulfolane, present in an amount of about 1 to 50% by weight of the composition, and the inert material, e.g., water, makes up the rest of the composition.

DETAILED DESCRIPTION OF THE INVENTION

The compound denatonium saccharide is believed to be the bitterest substance known; it exhibits a vile bittering and lingering taste effect even in a dilution ration of 1:100 million. Denatonium saccharide has the following chemical formula:

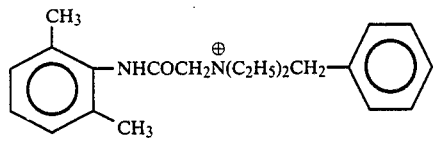

-continued

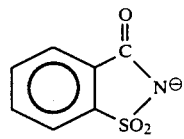

Its chemical name is:
N,N,N,N,-Benzyldiethyl[2-,6-xylylcarbomoyl)methyl-]ammonium saccharide.

Denatonium saccharide is prepared by heating equivalent amounts of a denatonium halide, e.g. denatonium chloride, with an alkali metal salt of saccharin, e.g. sodium saccharin, calcium saccharin, and so forth, in a solvent medium, e.g. water, at an elevated temperature, generally about 55°–65° C. The product is recovered in crystalline form by solvent extraction and precipitation. The starting material denatonium chloride is prepared by reacting the corresponding tertiary amine, lidocaine, with benzyl chloride.

Denatonium saccharide is essentially non-toxic, it has an $LD^{50}$ of 1500 mg/kg.

In accordance with the invention, compositions for utilizing the bitter tasting property of denatonium saccharide at low concentrations are provided herein. These compositions consist essentially of (a) an effective amount of denatonium sacchride, (b) a solvent which provides penetrating capability to the composition selected from dimethyl sulfoxide and 2,4-dimethylsulfolane and (c) an inert material therewith.

The denatonium saccharide suitably is present in a concentration of about 0.001 to 0.5% by wt. of the composition, preferably about 0.01 to 0.1% by wt., and, optimally, about 0.05% by wt. At these concentrations the denatonium saccharide is particularly effective in animal and rodent repellent applications.

The penetrating solvent suitably is present in an amount of about 1 to 50% by wt. of the composition, preferably about 5 to 20% by wt. and, optimally, about 10% by wt. of the composition. The preferred solvent in the composition of the invention is dimethyl sulfoxide which is capable of penetrating most surfaces to enhance the repellant properties of the composition.

The inert constituent of the composition usually is water, which makes up the remainder of the composition.

Optionally, the composition also may include one or more of desirable additive materials to increase the range of properties of the composition. For example, an essential oil may be included to provide the composition with a scent, especially those essential oils which possess animal repellent properties. Suitable essential oils include, but are not limited to, eucalyptus oil, thymol, menthol, mustard oil, and so forth. In addition, for specialized applications, alcohols, glycols, and polyols, for example, glycerol, may be included in an amount up to 20% by wt., preferably up to 10% by wt. of the composition, to enhance the applicability of the composition to surfaces and to reduce the freezing point of the solution. Similarly, surface active agents and hydrocarbons may be included for other surfaces. Humectants and thickeners also may be present, where necessary. The composition of the invention can be added to paints, pastes, glues, and the like.

The composition of the present invention with its special penetrating ingredient, will permeate plants, bark of trees, leaves, fences, telephone poles, furniture, garbage bags, ornamental plants, grass, sprouts, non-edible seeds, and the like.

The composition provides repellent protection against gnawing, biting, licking, and feeding damage caused by dogs, cats, beavers, rabbits, racoons, mice, rats, opossum, wolves, deer, elk, gophers, coyotes, squirrels, crows, woodpeckers, sea gulls, etc. It is effective against all animals with gustatory and olfactory sensitivity.

The composition may be applied to a surface in several ways. For example, it can be brushed on, or sprayed on, or painted on, or the surface to be protected may be dipped into it. When encapsulated into a tape, it can be pressed onto the surface. The composition itself may be present as a solution, emulsion, gel, paint, paste, cream, or encapsulate, as desired.

The following examples will more particularly illustrate the invention.

EXAMPLES

Preparation of Denatonium Saccharide

Denatonium chloride, 10 g. in 100 ml distilled water at 55°–65° C., was magnetically stirred and 7.94 g solid sodium saccharin was added to give an initially gelatinous oil which solidified on stirring. The solid was taken up in chloroform, the solution reduced to incipient dryness and the resulting oil was heated with 15 ml of isopropanol to give a solution to which was added 100 ml ethyl acetate to give a fine white powder, 11.76 g (80.5% yield) of denatonium scaaharide, m.p. 177°–8° C.

Denatonium Saccharide Compositions and Uses

A composition of 0.065% by wt. of denatonium saccharide, 9.9% by weight of dimethyl sulfoxide and the rest water to 100% is prepared by thoroughly mixing the ingredients. The composition is applied by spraying onto non-edible plants, leaves, cones, bark of trees, grass, fences, telephone poles, and the like to act as an animal and rodent repellent. The composition is noted to be particularly effective for this purpose even in an environment where such animals and rodents ordinarily attack the surfaces mentioned.

While the invention has been illustrated with certain embodiments thereof, modifications and change may be made which are within the skill of the art. It is intended to be bound only by the following claims.

What is claimed is:

1. A composition for utilizing the lingering bitter tasting property of denatonium saccharide at low concentration consisting essentially of:
    (a) an effective amount of denatonium saccharide,
    (b) a solvent which provides penetrating capability to the composition selected from dimethyl sulfoxide and 2,4-dimethylsulfolane, and
    (c) an inert material therewith.

2. A composition according to claim 1 wherein (a) and (b) are present in amounts of 0.001 to 0.5% and 1 to 50% by wt. respectively and (c) is the rest to 100%.

3. A composition according to claim 1 wherein (a) and (b) are present in amounts of 0.01 to 0.1% and 5 to 20% by wt., respectively, and (c) is the rest to 100%.

4. A composition according to claim 1 wherein (a), (b) and (c) are present in amounts of 0.065%, 9.935% and 90%, respectively.

5. A composition according to claim 1 which also includes one or more materials selected from an essential oil, an alcohol, a polyol, a glycol, a surface active agent, a humectant and a thickener.

6. A composition according to claim 1 wherein (b) is dimethyl sulfoxide.

7. A composition according to claim 1 wherein (b) is 2,4-dimethylsulfolane.

8. A composition according to claim 1 wherein (c) is water.

9. A composition according to claim 5 wherein said essential oil is eucalyptus oil, thymol, menthol, or mustard oil.

10. A composition according to claim 5 wherein said polyol or glycol is present in an amount up to about 20% by wt. of said composition.

11. A composition according to claim 5 wherein said polyol is glycerol present in an amount up to about 10% by wt. of said composition.

12. A method of protecting a surface against attack by animals which comprises applying the composition of claim 1 to said substance.

* * * * *